United States Patent [19]

Mastico et al.

[11] Patent Number: 5,534,257
[45] Date of Patent: Jul. 9, 1996

[54] ANTIGEN-PRESENTING CAPSID WITH FUSION MS2-COAT PROTEIN

[75] Inventors: Robert A. Mastico, Braintree, Mass.; Peter G. Stockley, Ilkley; Simon J. Talbot, Street, both of England

[73] Assignee: British Technology Group Limited, England

[21] Appl. No.: 90,148

[22] PCT Filed: Jan. 22, 1992

[86] PCT No.: PCT/GB92/00124

§ 371 Date: Nov. 8, 1993

§ 102(e) Date: Nov. 8, 1993

[87] PCT Pub. No.: WO92/13081

PCT Pub. Date: Aug. 6, 1992

[30] Foreign Application Priority Data

Jan. 24, 1991 [GB] United Kingdom ............... 9101550

[51] Int. Cl.$^6$ .................. A61K 39/116; A61K 39/12; C07K 14/195; C12N 7/01
[52] U.S. Cl. ................... 424/192.1; 424/184.1; 424/234.1; 424/204.1; 424/201.1; 424/203.1; 435/69.3; 435/172.3; 435/235.1; 435/320.1; 514/2; 536/23.1; 536/23.72; 530/350; 530/825; 530/826
[58] Field of Search ................ 424/88, 89, 184.1, 424/192.1, 234.1, 204.1, 201.1–203.1; 435/69.3, 172.1, 172.3, 235.1, 252.3, 320.1; 514/2; 536/23.1, 23.4, 23.72, 23.7; 530/350, 403, 825, 826

[56] References Cited

FOREIGN PATENT DOCUMENTS

| 353814 | 2/1990 | European Pat. Off.. |
|---|---|---|
| 398332 | 11/1990 | European Pat. Off.. |
| WO8910967 | 11/1989 | WIPO . |
| WO9002187 | 3/1990 | WIPO . |

OTHER PUBLICATIONS

Bowie, J. V. et al. Science 247: 1306–1310 (1990).
Kumar, V. et al. Proc. Natl. Acad. Sci USA 87: 1337–1341 (1990).
de la Cruz et al. J. Biol. Chem. 263 (9): 4318–4322 (1988).
Smith, G. P. Science 228: 1315–1317 (1985).
Peabody, D. S. J. Biol. Chem. 265(10): 5684–5689 (1990).
Kozcovskaya, T. M. et al. J. Uol. Biol (USSR) 584–593 (1988).
Chem. Abst., 72, (1970), 107087x.
Reisnier et al, Thrombosis and Haemostasis, 58, No. 1 (1987) 353, Abstract.

Primary Examiner—Hazel F. Sidberry
Assistant Examiner—Michael Tuscan
Attorney, Agent, or Firm—Rosenman & Colin

[57] ABSTRACT

A chimaeric protein, suitable for incorporation in a vaccine and capable of forming parts of a capsid assembly, comprises the amino acid sequence of the coat protein of phage MS-2, or a conservatively modified variant thereof, or sufficient of said sequence or variant to retain capsid-forming capability, which amino acid sequence has been modified by insertion of a foreign epitope in the region corresponding to a protuberant protein hairpin in the capsid assembly as shown in the crystal structure of the intact phage.

4 Claims, 4 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 129 AMINO ACIDS
( B ) TYPE: AMINO ACID
( D ) TOPOLOGY: Not Relevant ( i i ) MOLECULE TYPE: PROTEIN ( v i ) ORIGINAL SOURCE:
( A ) ORGANISM: VIRUS ( i x ) FEATURE:
( A ) NAME/KEY: Coat protein from MS2- RNA bacteriophage
( B ) LOCATION: Location 1 through 129 below represents entire MS2 coat protein in the published sequence.

( x ) PUBLICATION INFORMATION:
( A ) AUTHORS: Min Jou, W.; Haegeman, G.; Ysebaert, M.; Fiers, W.
( B ) TITLE: Nucleotide sequence of the gene coding for the bacteriophage MS2 coat protein
( C ) JOURNAL: Nature
( D ) VOLUME: 237
( F ) PAGES: 82-88
( G ) DATE: 1972

( x i ) SEQUENCE DESCRIPTION: SEQ ID NO: 1:

```
Ala Ser Asn Phe Thr Gln Phe Val Leu Val
                 5                   10

Asp Asn Gly Gly Thr Gly Asp Val Thr Val
                15                   20

Ala Pro Ser Asn Phe Ala Asn Gly Val Ala
                25                   30

Glu Trp Ile Ser Ser Asn Ser Arg Ser Gln
                35                   40

Ala Tyr Lys Val Thr Cys Ser Val Arg Gln
                45                   50

Ser Ser Ala Gln Asn Arg Lys Tyr Thr Ile
                55                   60

Lys Val Glu Val Pro Lys Val Ala Thr Gln
                65                   70

Thr Val Gly Gly Val Glu Leu Pro Val Ala
                75                   80

Ala Trp Arg Ser Tyr Leu Asn Met Glu Leu
                85                   90

Thr Ile Pro Ile Phe Ala Thr Asn Ser Asp
                95                  100
```

```
Cys Glu Leu Ile Val Lys Ala Met Gln Gly
                105                 110

Leu Leu Lys Asp Gly Asn Pro Ile Pro Ser
                115                 120

Ala Ile Ala Ala Asn Ser Gly Ile Tyr
                125             129
```

( 2 ) INFORMATION FOR SEQ ID NO:2:

( i ) SEQUENCE CHARACTERISTICS:
        ( A ) LENGTH: 9 AMINO ACIDS
        ( B ) TYPE: AMINO ACID
        ( D ) TOPOLOGY: Not Relevant     ( i i ) MOLECULE TYPE: PEPTIDE     ( x i ) SEQUENCE DESCRIPTION: SEQ ID NO: 2:

```
Tyr Pro Tyr Asp Val Pro Asp Tyr Ala
                5                 9
```

( 2 ) INFORMATION FOR SEQ ID NO:3:

( i ) SEQUENCE CHARACTERISTICS:
        ( A ) LENGTH: 10 AMINO ACIDS
        ( B ) TYPE: AMINO ACID
        ( D ) TOPOLOGY: Not Relevant     ( i i ) MOLECULE TYPE: PEPTIDE     ( x i ) SEQUENCE DESCRIPTION: SEQ ID NO: 3:

```
Phe Gly Phe Phe Gly Ser Gly Lys Thr Lys
                5                     10
```

( 2 ) INFORMATION FOR SEQ ID NO:4:

( i ) SEQUENCE CHARACTERISTICS:
        ( A ) LENGTH: 14 AMINO ACIDS
        ( B ) TYPE: AMINO ACID
        ( D ) TOPOLOGY: Not Relevant     ( i i ) MOLECULE TYPE: PEPTIDE     ( x i ) SEQUENCE DESCRIPTION: SEQ ID NO: 4:

```
Asn Asn Thr Arg Lys Ser Ile Arg Ile Gln
                5                     10

Arg Gly Pro Gly
            14
```

( 2 ) INFORMATION FOR SEQ ID NO:5:

( i ) SEQUENCE CHARACTERISTICS:
        ( A ) LENGTH: 13 AMINO ACIDS
        ( B ) TYPE: AMINO ACID
        ( D ) TOPOLOGY: Not Relevant     ( i i ) MOLECULE TYPE: PEPTIDE     ( x i ) SEQUENCE DESCRIPTION: SEQ ID NO: 5:

```
Gly Pro Gly Arg Ala Phe Val Thr Ile Gly
                5                     10

Lys Ile Gly
        13
```

( 2 ) INFORMATION FOR SEQ ID NO:6:

( i ) SEQUENCE CHARACTERISTICS:

( A ) LENGTH: 24 AMINO ACIDS
( B ) TYPE: AMINO ACID
( D ) TOPOLOGY: Not Relevant ( i i ) MOLECULE TYPE: PEPTIDE ( x i ) SEQUENCE DESCRIPTION: SEQ ID NO: 6:

| Asn | Asn | Thr | Arg | Lys | Ser | Ile | Arg | Ile | Gln |
|---|---|---|---|---|---|---|---|---|---|
| | | | | 5 | | | | | 10 |
| Arg | Gly | Pro | Gly | Arg | Ala | Phe | Val | Thr | Ile |
| | | | | 15 | | | | | 20 |
| Gly | Lys | Ile | Gly | | | | | | |
| | | | 24 | | | | | | |

ANTIGEN-PRESENTING CAPSID WITH FUSION MS2-COAT PROTEIN

This invention relates to an antigen-presenting chimaeric protein and is particularly directed to virus proteins containing foreign epitopes, the preparation of such proteins and their use as vaccines.

The growth of recombinant DNA technology in recent years has led to the introduction of vaccines in which an immunogenic protein has been identified, cloned and expressed in a suitable bacterial host to obtain sufficient quantities of protein to allow effective protective immunisation in both animals and humans. As an extension of such techniques, it has been proposed to incorporate only the immunogenic epitopes in carrier proteins capable of expression in a suitable host while retaining the immunising properties of the epitope. Thus Beesley et al., Biotechnology, 8, 1990, 644–649, describe the preparation of chimaeric proteins in which epitopes of foot and mouth disease virus or human chorionic gonadotrophin are fused to the N-terminus of hepatitis B core protein as carrier. Expression of the chimaeric protein was carried out in yeast, as expression in E. coli was found to be not wholly satisfactory.

It has also been suggested by Pushko et al., Abstracts of VIIIth International Congress of Virology, Berlin, Aug. 26–31 1990, P38-006, that certain unidentified regions of the RNA-phage fr coat protein capsid may be capable of accepting foreign amino acid sequences without loss of capsid-forming ability. However, these workers give no indication of anything other than randon insertion of such amino acid sequences throughout the coat protein so as to obtain certain unidentified chimaeric constructs.

There is clearly a need in the furtherance of vaccine technology for production of chimaeric proteins capable of efficient and reproducible presentation of foreign immunogenic epitopes, which proteins can be made by recombinant methods involving expression in a well understood and regulatable bacterial host such as E. coli. Natural viral epitopes are of course presented on the regular surface lattice of viral shells or membranes. A system which mimics this natural form of antigen presentation should, in theory, prove particularly efficient in eliciting the immune response. However, to achieve such a result, it is necessary to identify bacterial virus coat proteins which can be cloned and when expressed form capsids independently of the genetic material of the virus. Furthermore, it is necessary to identify a particular region of the coat protein which is not essential to capsid formation and which can be manipulated independently of the remainder of the protein so as to receive the foreign epitope.

It has now been found that eptiope insertion in an identified class of virus protein carriers can be specifically directed so that foreign epitopes are reliably presented on the surface of the protein capsid assembly after the expression of the chimaeric protein in a bacterial host.

It was by no means predictable that such a result could be achieved. Not all viruses possess coat proteins which will self assemble: furthermore it is not possible to predict such self assembly. Even further, unlike animal viruses, bacterial viruses cannot naturally be expected to possess immunodominant regions and there is thus no guidance as to which region of a bacterial virus coat protein (if any) could be modified in the reasonable expectation of inducing an immune response.

According to the present invention there is provided a chimaeric protein, capable of forming part of a capsid assembly and comprising the amino acid sequence of the coat protein of phage MS-2, or a conservatively modified variant thereof, or sufficient of said sequence or variant to retain capsid-forming capability, which amino acid sequence has been modified by insertion of a foreign eptiope in the region of the protein corresponding to an N-terminal β-hairpin, as determined by X-ray crystallography of the whole phage particle.

Surprisingly, it has been found that such a chimaeric protein can be expressed in a suitable bacterial host to yield capsids empty of the phage RNA and largely free of other nucleic acid contaminants.

The chimaeric coat protein is preferably that derived from phage MS-2, but it may also be derived from related RNA-phages capable of replication in E. coli, such as phages R17, fr, GA, Qβ and SP. Such RNA-phages of physical structure similar to that of MS-2 will contain some chemical variation in the amino acid residues of the coat protein and are thus conservatively modified variants of MS-2 coat protein. While it is believed at present that substantially the entire coat protein may be required for capsid assembly, deletions and/or insertions of a relatively minor nature may also be possible whilst still retaining capsid-forming capability. Proteins having such modified sequences are included within the scope of the invention.

As stated above, the foreign eptiope is inserted at the region of the protein which in the assembled capsid corresponds to the N-terminal β-hairpin. The three-dimensional structure of the MS-2 phage particle has been published by Valegård et al., (Nature, 1990, 345, 36–41). The published data show that, firstly, the structure of the coat protein is not related to the eight-stranded β-barrel motif found in all other spherical RNA virus subunits whose structures are known at the present time. Secondly, although the coat protein exhibits quasi-equivalent inter-subunit contacts, there are no other devices, such as extended arms of polypeptide, helping to secure each protein conformer. The coat protein structure can be viewed in terms of three separate regions. These are not domains in the usual sense but could represent independent folding units. These regions are residues 1–20, which form the β-hairpin structure which protrudes from the surface of the phage forming the most distal radial feature. This region is followed by residues 21–94 which form five β-strands including the "FG-loop" which is the site of the only major conformational change between quasi-equivalent conformers. These β-strands are then followed by two α-helices, residues 95–125, which interdigitate to secure dimers of the cost protein sub-units. Valegået al. are concerned solely with the physical structure of the MS-2 virus and do not attempt to elucidate the mode of action of the virus.

As explained above, the present invention comprises modification of the coat protein amino acid sequence by introduction of a foreign epitope in the region corresponding to the protruberant hairpin. The chimaeric protein of the invention has therefore been so modified in the region of amino acid residues 1 to 20, such numbering being with reference to the entire cost protein sequence of MS-2 as published by Fiers, Nature, 1976, 260, 500–507, the disclosure of which is incorporated herein by, reference thereto. Preferably the modification to insert the foreign epitope is towards or at the middle of the hairpin region. It is particularly preferred to introduce the foreign epitope in the region of the glycine 14 and threonine 15 residues of the cost protein. Although not wishing to be bound by any particular theory, it is postulated that the presence of one or more glycine residues immediately flanking the inserted epitope is advantageous in introducing conformational flexibility to the epitope in its subsequent presentation.

The foreign inserted epitope may vary widely dependant on the immunogenic properties desired in the chimaeric protein. Thus, according to one form of the invention, a 9-mer peptide sequence derived from the haemagglutinin of the human pathogen influenza virus (or a haemagglutinin moiety containing the epitope) is engineered into the MS-2 coat protein. Alternatively a decapeptide from the heavy chain of IgE, useful in vaccination against IgE-mediated allergic reactions or a decapeptide related thereto may be introduced. Such a decapeptide is described and claimed in international Patent Application Publication No. WO90/15878. While comparatively short sequences having only a few amino acid residues may be inserted, it is also contemplated that longer epitopes, for example of 30 or more residues, may be inserted, for example an epitope of about 24 residues containing the identified 8-mer lmmunodominant sequence of gp120 from human HIV 1 virus. It will be appreciated that the maximum length of epitope and the nature of the epitope will depend on the resulting chimaeric protein retaining its ability to form a capsid assembly. Multiple copies or a mixture of epitopes, especially of short epitopes, may be introduced so long as capsid forming ability is retained, and the invention is intended to include the introduction of multiple copies of a foreign epitope or plurality of foreign epitopes in the region of the N-terminal β-hairpin of the coat protein. Epitopes from other pathogens of importance in human and veterinary medicine are also contemplated for insertion, for example derived from FHDV VPI protein or HIVp24. It will be appreciated that the inserted epitope may be bounded at one or both ends by additional amino acids which are not essential to the epitopic function of the insert. Further the term 'epitope' is intended to include precursor inserts which can exhibit their epitopic function after post translational modification.

The invention also extends to capsid assemblies of the chimaeric proteins of the invention. It has been found that such capsids can be expressed in $E. coli$ as "phage empties" without the RNA of the live virus. The generation of mixed capsid assemblies is contemplated, for example by prior disassembly of in vivo assembled homogeneous samples followed by reassembly of a mixture. Such capsid assemblies are intended, for example, to be capable of raising a mixed immune response and thus capable of finding application as vaccines for immunisation against a natural spectrum of viral epitopes in population. The invention therefore also extends to vaccines comprising one or more chimaeric proteins as defined above.

The chimaeric proteins of the invention may be produced by introduction of the cDNA sequence corresponding to the coat protein of MS-2 (or the cDNA sequence corresponding to a conservatively modified variant of such a coat protein or sufficient of said protein or variant to retain capsid-forming capability) into a sequencing vector suitable for site directed mutagenesis, creation of a unique restriction enzyme recognition site in the region of the cDNA coding for the protruberant hairpin, introduction of oligonucleotides encompassing the foreign epitope at the restriction site (by conventional genetic engineering techniques) and sub-cloning the thus modified gene into a suitable expression vector, followed by induction of expression from the modified expression vector carrying the foreign gene in a suitable host. A suitable host for MS-2 is $E. coli$, which is advantageous in that fermentations are comparatively easy and cheap to perform and the system is well understood. Alternatively, expression may be carried out in a heterologous host such as yeast which may allow post-translational processing of inserted sequences.

Preferably, the restriction enzyme recognition site is created at the cDNA codons corresponding to glycine 14 and threonine 15, with reference to the amino acid sequence of the coat protein of MS-2. Suitably a Kpn 1 recognition site is created. Such a site has been found to be particularly suitable in that digestion with Kpn 1 and subsequent ligation in the presence of the foreign oligonucleotide results in in-frame insertion of the epitope, flanked at both ends by a glycine and threonine residue, which, it is believed, enhances the conformational flexibility of the epitope and, when presented in vivo, this should assist in immune recognition.

The sequencing vector may be any of those Known for site directed mutagenesis, such as M13 mp 18. The cDNA is obtained from the RNA of MS-2 by standard reverse transcription techniques. The starting RNA of MS-2 may be obtained by growing the organism or from a commercial sample (available from Boehringer Mannhelm, Germany). The expression vector used for expression in $E. coli$ is suitably pGW11 together with the necessary promoter/inducer such as a tac promoter induced by IPTG.

Following expression $E. coli$, the overexpressed cellular proteins are subjected to purification procedures to obtain the MS-2 derived coat protein. A suitable purification protocol comprises sonication to release soluble cellular proteins, centrifugation, treatment of the resulting supernatant with DNase I, ammonium sulphate precipitation, dialysis and size fractionation to obtain assembled capsids and such techniques as immuno-affinity chromatography. The purification protocol may require modification dependent on the chemical and physical nature of the introduced foreign epitope. The resulting capsids may be characterised by gel filtration and/or sucrose density gradient techniques and the identity of the insert confirmed by sequencing. It has been found that it is possible to obtain essentially homogeneous coat protein as empty capsids, as shown by electron microscopy and protein sequencing, and these capsids have also been crystallized.

Those capsids into which a foreign epitope has been introduced have been shown by Western blot techniques to react both with a monoclonal antibody to the foreign epitope and with a polyclonal serum containing antibodies to the wild type coat protein, while wild type capsids react only to the polyclonal serum.

The chimaeric proteins and assembled capsids of the present invention are envisaged for employment as vaccines in any of the ways usual in that art.

Thus, for example, it is contemplated that the capsids may be employed an aqueous suspension with or without the presence of an adjuvant and/or additional enhancing fractions, for application by injection or protected oral delivery. Suitable adjuvants are those conventionally used in human and veterinary vaccines, such as incomplete Freunds adjuvant, the aluminum hydroxide gel adjuvant "Alhydrogel" (a registered Trade Mark) or Saponin. Alternatively the vaccine may be formulated as a slow release capsule. Additional materials may be included to enhance immune recognition, such as muramyl dipeptide.

While it will be appreciated that the size and frequency of the immunising doses will vary considerably dependent on the field of application (human or veterinary) and the pathogen against which protection is desired, a typical vaccine may employ from 0.2 to 5 mg of capsids, suitably about 0.5 mg, the intention being, for example, to administer the vaccine in from 1 to 3 doses at 2 to 4 week intervals. Such doses are intended to illustrate the invention and are not intended to be in any way limiting.

Taking the 9-mer derived from influenza virus described above as an example, it is contemplated that a typical patient would be immunised by administration of 0.2 to 5 mg protein, either in aqueous suspension or after admixture with an adjuvant such as aluminum hydroxide suspension, either as a single dose or multiple doses at intervals of, for example, 2 weeks. Any suitable inoculation route may be practised, e.g. subcutaneous (s.c.), intramuscular or intradermal. Alternatively a tablet of suitably coated material (to protect against gastric digestion) may be given to stimulate immunity at the gut mucosal surface.

It will be apparent that there are several advantages in using MS-2 and related phages as an antigen presentation system. Thus the empty coat protein capsids can be readily expressed in comparatively high yield in E. coli, the product is easily purified and it has been found that the assembled capsids show considerable stability with respect to a range of temperatures, pH and ionic strength. While not wishing to be bound by any particular theory, it is postulated that the invention also allows one to present epitopes in a regular array on the surface of carrier capsids, at predetermined locations, which will maximise immune recognition, which relies on the multidentate nature of antibody molecules.

It is believed that the MS-2 system has considerable potential utility for the presentation of foreign peptide sequences on the surface of a spherical bacteriophage. The system has a number of advantages over the filamentous bacteriophage alternatives. The MS-2 coat protein is capable of facile self-assembly in the absence of nucleic acid unlike the filamentous phages in which assembly is concomitent with encapsidation of nucleic acid. Furthermore, the filamentous coat protein must undergo a post translational processing and membrane insertion before assembly occurs whereas the MS-2 protein is unprocessed. The MS-2 system also has the advantage of a detailed molecular mode for the coat protein a following the effects of foreign peptide insertion to be modelled. The apparent ability of MS2 chimeras to produce specific titres against defined conformations of epitopes suggests that they offer a cheap and elegant method for the production of refined vaccines.

The following Examples illustrate the invention.

Example 1

Presentation of epitope derived from influenza virus.
a) Preparation of expression vector including coat protein cDNA from MS-2.

The coat protein of MS-2 was obtained by growing phage MS-2, purifying the RNA, followed by oligonucleotide primer directed reverse transcription to produce single-stranded cDNA which was converted to double stranded cDNA using oligo primers and Klenow polymerase. The cDNA was then subcloned into an expression vector (pGN11), placing the coat protein under the control of the inducible tac promoter.

b) Preparation of modified expression vector including foreign epitope.

The cDNA of the MS-2 coat protein (obtained as in a) above) was sub-cloned from expression vector pGW11 into standard sequencing vector M13mp18, to produce a single strand substrate for site directed mutagenesis. A Kpn 1 restriction site was introduced by modifying the DNA codons corresponding to glycine 14 and threonine 15 of the MS-2 coat protein. A nucleotide sequence corresponding to a 9-mer peptide sequence derived from the haemagglutinin of the human pathogen influenza virus was introduced by digestion with Kpn 1 and subsequent ligation. The thus modified gene was sub-cloned into a suitable expression vector (pGW11). The oligonucleoitde encoded the 9-mer amino acid sequence YPYDVPDYA, SEQ. ID No: 2 identified as containing one of the antigenic determinants by Wilson et al., (Molecular and Cell Biology, May 1988, 2159–2165 and Cell, Vol. 37, 1984, 767–778). The oligonucleotide site-directed mutagenesis described above to construct the Kpn 1 site was carried out using standard commerically available kits. Further DNA manipulations were carried out using standard techniques (Maniatis et al., "Molecular Cloning. A laboratory manual", 2nd Edition, (1989), Cold Spring Harbor Press, CSH, New York).

The resulting vector was sequenced to demonstrate the insertions of the codons for the 9-mer. As a consequence of the use of the Kpn 1 site, two additional codons, for glycine and threonine, were created downstream of the insert, i.e. a total insertion of 11 codons.

c) Expression of vectors in E. coli.

The pGH11 expression vectors with and without introduction of the foreign epitope codons were expressed in E. coli and the cellular proteins obtained, purified and characterised as follows:

Standard laboratory strains of E. coli were transformed ampicillin resistance) with the expression plasmid carrying the recombinant MS2 coat protein gene. Rapidly growing cultures of these transformants in rich media were induced by addition of IPTG to a final concentration of 1 mM when the O.D.$_{600}$ of the culture was between 0.4–0.6. Cell growth was continued overnight before the cells were harvested by centrifugation, resuspended in neutral buffer, sonicated to lyse the cells, followed by centrifugation to separate the supernatant (containing the expressed recombinant products) and cellular debris. The supernatant was fractionated by ammonium sulphate precipitation, the pellet of product being resuspended in buffer before being purified on the basis of size by either sucrose density gradients or gel filtration chromatography or by immuno-affinity chromatography. The modified coat protein is referred to hereinafter as MS2-HA. Its sequence was confirmed by N-terminal amino acid sequencing over the first 30 residues.

EXAMPLE 2

Presentation of epitope related to human IgE. Using the techniques described in a), b) and c) of Example 1, a decapeptide related to a sequence from human IgE responsible for triggering degranulation of mast cells as described in International Patent Application Publication No. WO90/15878, was inserted in MS-2 coat protein and expressed and purified. The oligonucleotide inserted at the Kpn I restriction site encoded the 10-mer amino acid sequence F G F F G S G K T K, SEQ. ID No: 3, the modified coat protein being referred to hereinafter as MS2-IgE' because of its relationship to the IgE decapeptide. As described in Example 1, as a consequence of the use of the Kpn I site, two additional codons, for glycine and threonine, were created, leading to a total insertion of 12 amino acids. The IgE'-modified MS-2 coat protein was identified and its activity tested as described below. N-terminal amino acid sequencing over the first 30 residues confirmed the sequence for the insert.

EXAMPLE 3

Presentation of epitope derived from HIVgp120.

Using the techniques described in Example 1, with modification as described below, a 24-mer derived from the V3 loop of gp 120 from Human Immunodeficiency Virus (HIV-1) was incorporated in MS-2 coat protein and expressed and purified. The gp 120 insert was generated by first annealing oligonucleotides encoding the amino acid sequences N N T R K S I R I Q R G P G, SEQ ID No. 4, and G P G R A F V T I G K I G, SEQ ID No. 5, treating with Klenow polymerase to make double-stranded, $T_4$ polynucleotide kinase and DNA ligase to produce tandemly ligated fragments, which were then digested with Kpn I before gel-purification and cloning into suitably prepared aliquots of the expression vectors. The inserted 24-mer amino acid sequence was N N T R K S I R I Q R G P G R A F V T I G K I G, SEQ ID No. 6; and the resulting modified coat protein is referred to hereinafter as MS2-gp 120. Again it is to be noted that, as a consequence of the use of the Kpn I site, two additional codons were created, leading to a total insertion of 26 amino acids. The gp 120 modified MS-2 coat protein was identified as described below.

EXAMPLE 4

Immune response of MS2-HA.

The immune response of the modified coat protein obtained in accordance with Example 1, and purified by centrifugation through sucrose density gradients, was investigated as follows:

Coat protein samples with and without the insertion of the foreign eptiope were subjected to Western blotting and probed with the following antibodies:

i) a polyclonal serum containing antibodies to wild type MS2 coat protein obtained from New Zealand white rabbits immunised in the presence of complete Freund's adjuvant with purified monomeric MS-2 coat protein purified from the intact phage.

ii) a mouse anti-peptide monoclonal antibody to the 9-mer (12CA5-obtainable from the Research Institute, of Scripps Clinic, California, USA).

The procedure employed was as follows:

Coat protean samples with and without the 9-mer insert were subjected to SDS-PAGE and then transferred onto nitrocellulose paper. The Western blot was then probed with either i) or ii) and visualised with horseradish peroxidase—conjugated goat anti-rabbit or rat anti-mouse IgG respectively, using the method of Harlow and Lane, "Antibodies: A Laboratory Manual" (1988), Cold Spring Harbor Laboratory, New York.

The polyclonal serum i) reacted with both samples of coat protein, with only minor cross-reaction to other protein components and to a sample of purified influenza haemagglutinin. However, the monoclonal antibody ii) reacted essentially only with the coat protein band containing the 9-mer peptide epitope. This confirms the presence of the epitope coat protein material which is capable of self assembly in vivo and is entirely consistent with the mobility of the protein samples on SDS-PAGE where the wild type protein migrates slightly faster than the chimaeric 9-mer protein.

EXAMPLE 5

Identification of chimeric MS-2 proteins.

A) SDS-PAGE and Western blot analysis.

500ml cultures of *E. coli* (TG 1) carrying the appropriate pGW11 expression vectors, with and without introduction of foreign eptiope codons, were grown to O.D.$_{600}$ approximately 0.4 to 0.6 at 37° C., induced by addition of solid IPTG to 1 mM and incubation continued overnight. The cells were harvested by centrifugation and the pellets resuspended with 2–3× volume in 50 mM Tris-HCl+0.5% w/v Sarkosyl pH 6.5, then the cells were disrupted by sonication. The total sonicates were loaded on to SDS-PAGE (16.5% T:6% C) acrylamide gels according to the procedures of Sh ägger and Jagow (Anal. Biochem. 166, 368–379). Electrophoresis was performed at 95 V for 8–10 hrs and the acrylamide gels then stained with a 0.5% w/v Coomassie Blue R250 solution in methanol:acetic:water (2:0.2:3) for 8 hrs, then destained in the same solution but without the addition of dye.

Figure 1:
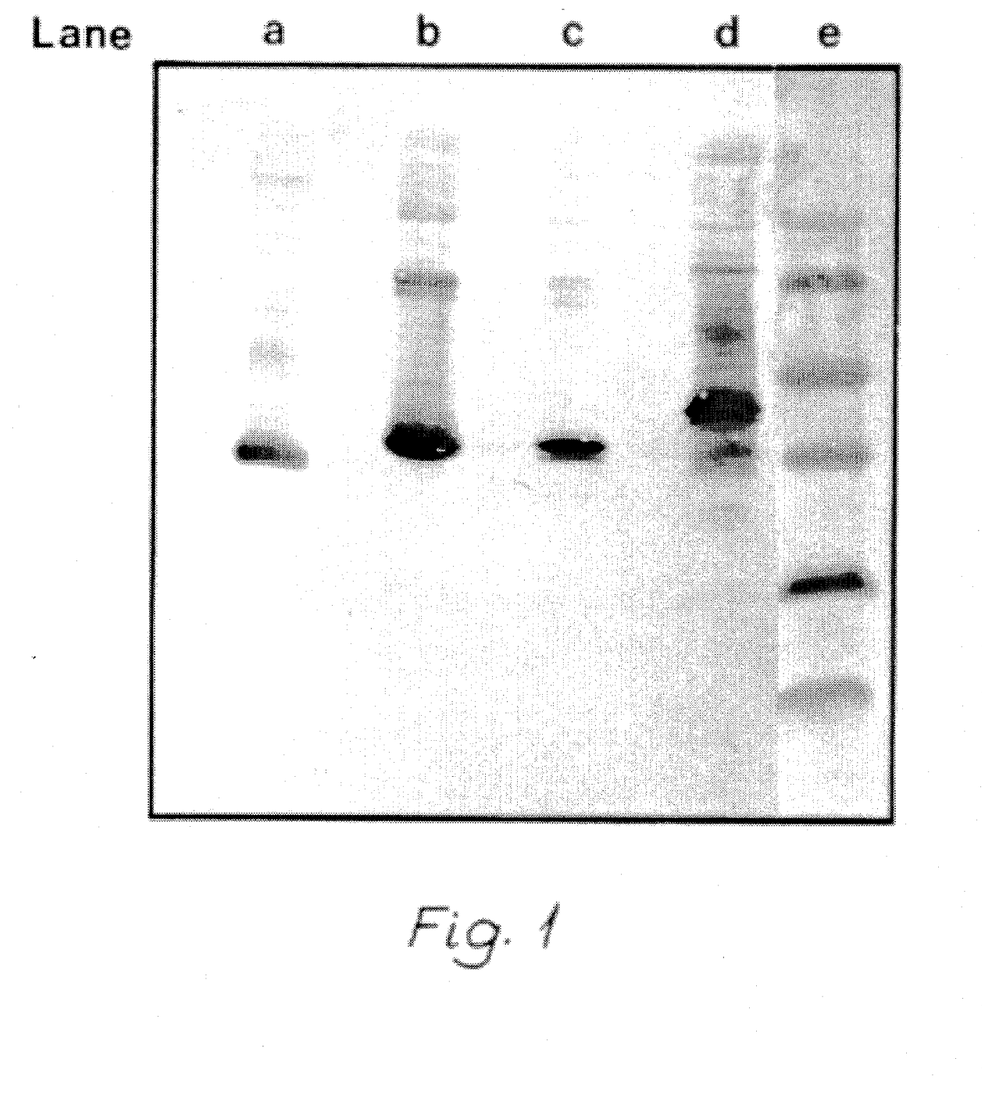
FIG. 1. Western Blot analysis using anti-MS-2-coat protein rabbit polyclonal antibody. Lane a) wild type MS-2 coat protein; lane b) MS-2HA; c) MS-2IgE'; d) MS-2gp120; lane e) molecular weight markers representing 43, 29, 28, 24, 6.2 and 4.3 kDa.

The results confirmed that in each case the major induced polypeptide band corresponded to the expected molecular weight for MS2 coat protein and the prepared chimeras. Gels equivalent to those prepared as described immediately above were blotted onto 0.2 μm nitrocellulose membrane according to the procedures of Harlow and Lane ("Antibodies: A Laboratory Manual" (1988), Cold Spring Harbor Laboratory, New York) and the proteins visualised by treatment with an anti-MS2-coat protein rabbit polyclonal antibody followed by horseradish peroxidase-conjugated goat anti-rabbit IgG. The results are shown in FIG. 1 where lane a) shows wild type MS-2 coat protein, lane b) shows MS2-HA, lane c) shows MS2-IgE' and lane d) shows MS2-gp 120. Lane e) is included as a molecular weight marker track (commercially available BRL Ltd.) with distinct bands representing 43, 29, 18, 14, 6.2 and 3.4 kDa molecular weights respectively.

Western blots were prepared as above and MS2-HA and MS2-IgE' transfers probed with either a mouse or rat monoclonal antibody directed to the HA 9-mer or the IgE 10-mer (related to the inserted IgE' 10-mer) respectively. These monoclonals were obtained from Dr. I. A. Wilson, Scripps Research Institute, La Jolla, Calif. or Dr. D. R. Stanworth, University of Birmingham, UK, respectively. The MS2-gp 120 transfer was probed with goat polyclonal anti gp 120 (obtained from Repligen Corp., Boston, USA). For visualisation, horseradish peroxidase conjugated to rabbit anti-mouse IgG, anti-rat or anti-goat IgG, was used respectively. The results showed specific immuno-reactivity towards the expected chimera. It is to be noted that the anti-IgE monoclonal antibody did cross react with the MS2-IgE' chimera.

B) Electron micrography.

Cells were prepared as in A) above but with the following changes:

The cells were grown at 30° C. The initial supernatant was dialysed directly against 20 mM sodium phosphate, pH 7.4 at 4° C. before being applied to an immuno-affinity column, which was then rinsed extensively with dialysis buffer, and then the same buffer+100 mM NaCl before the MS2 proteins were eluted in 20 mM acetic acid, 200 mM NaCl. The eluted proteins were immediately adjusted to pH 7.0 with 1M Tris-HCl, pH 9.0, concentrated by ammonium sulphate precipitation, resuspended in 10 mM Tris-HCl, 100 mM NaCl, pH 7.0 and then dialysed against the same buffer before being prepared for electron microscopy using the negative staining protocol of Sugiyama et al., (J. Mol. Biol., 166, 1967, 368–379). Micrographs were produced using a JEM-1200 Instrument at an accelerating voltage of 75 kV.

The immuno-affinity column consisted of affinity purified rabbit anti-MS2-CP polyclonal IgGs covalently coupled to Affigel-HZ™ (BioRad) according to the manufacturers instructions.

Figure 2:
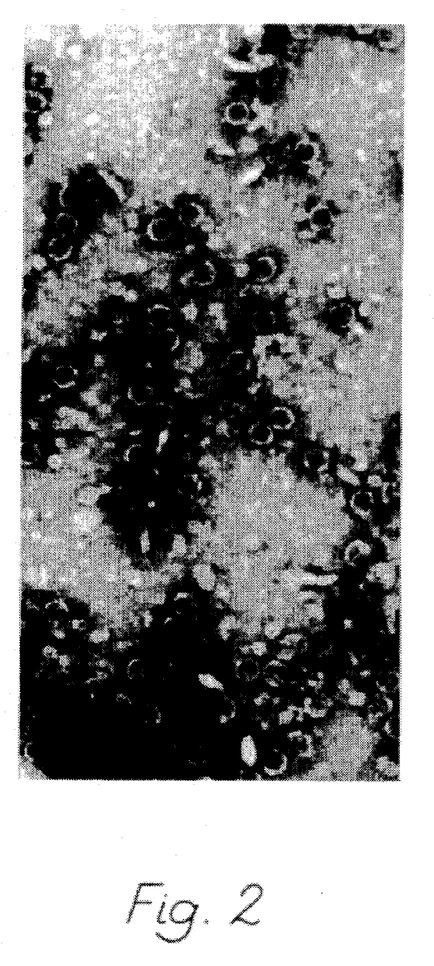
FIG. 2. Electron micrograph of wildtype MS-2 capsids.
Figure 3:
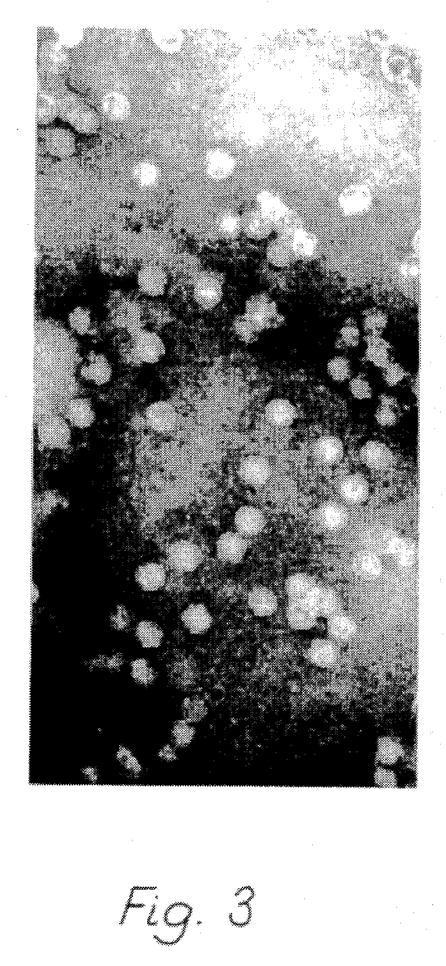
FIG. 3. Electron micrograph of MS-2HA capsids.
Figure 4:
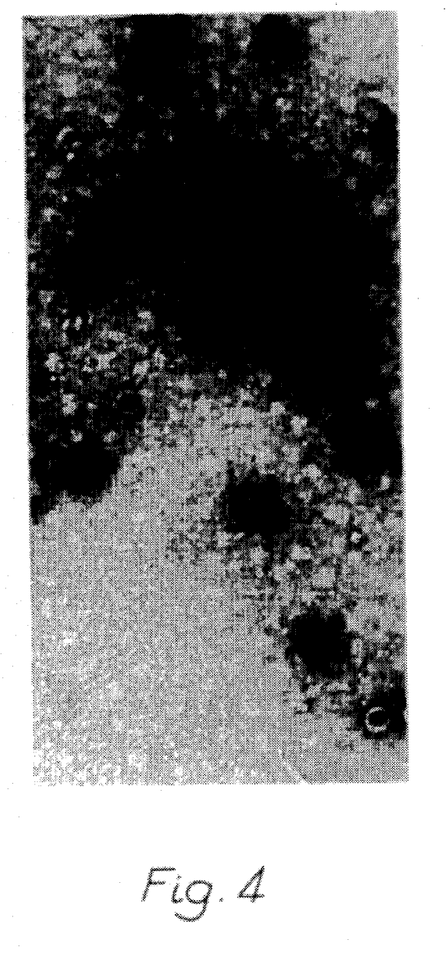
FIG. 4. Electron micrograph of MS-2IgE' capsids.
Figure 5:
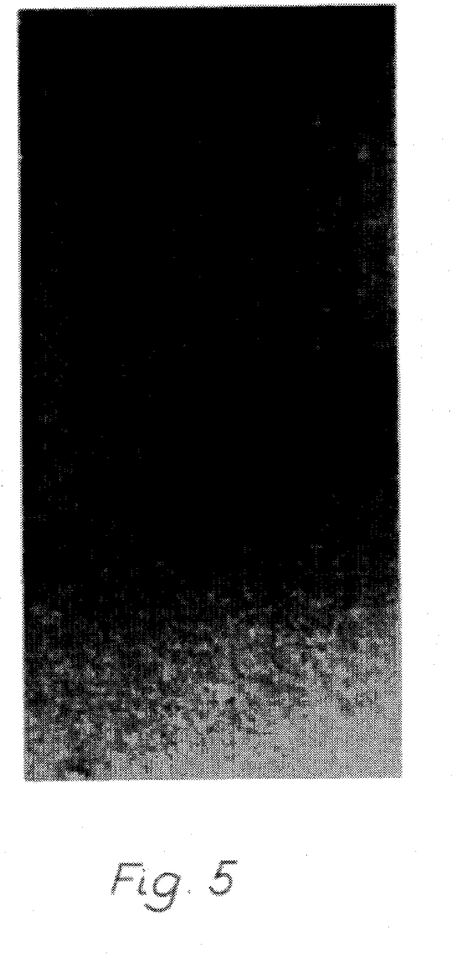
FIG. 5. Electron micrograph of MS-2gp120 capsids.

The results are shown in FIGS. 2 to 5 where FIG. 2 shows wild type MS2 capsids, FIG. 3 shows MS2-HA capsids, FIG. 4 shows MS2-IgE' capsids and FIG. 5 shows MS2-gp 120 capsids.

EXAMPLE 6

Antigenicity of MS2-HA. in vivo.

In order to test the immunogenicity of the MS2-HA construct in mice, MS2-HA was obtained as described in Example 1 and purified over sucrose density gradients, i.e. from the soluble supernatant of the initial cell fractionation.

Figure 6:
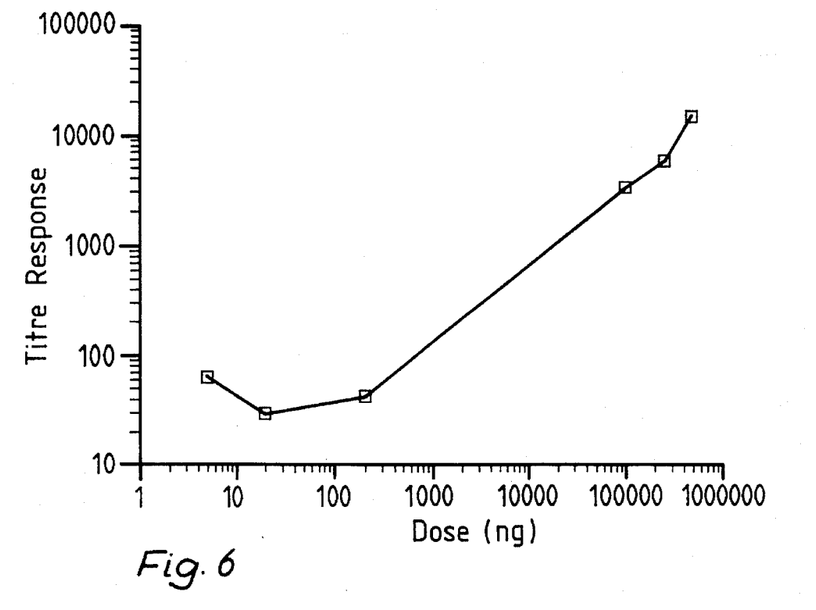
FIG. 6. Dose response curve of the 42 day titer against MS-2HA as measured by ELISA using MS-2HA as the antigen.

Pooled fractions containing the assembled MS2-HA were precipitated with ammonium sulphate, the precipitate collected by centrifugation and then resuspended in the buffer of choice (or stored at −20° C.). Groups of mice (TUXCS Number One) were immunised s.c. with a range of doses from 5 ng to 500 μg of total construct (the inserted HA9-mer is 9/140 by weight of this dose). Doses contained adjuvant (Alhydrogel) as a 1:1 mix. Booster doses were given at 7 or 14 day intervals, after removing a sample of blood for analysis. Even with the lowest doses there was some immunoreactivity as measured by ELISA assay versus MS2-HA (i.e. "self") as the antigen. However, significant responses were seen only for the larger doses and were still increasing after 42 days. A dose response curve for the 42 day titres is shown in FIG. 6.

Figure 7:
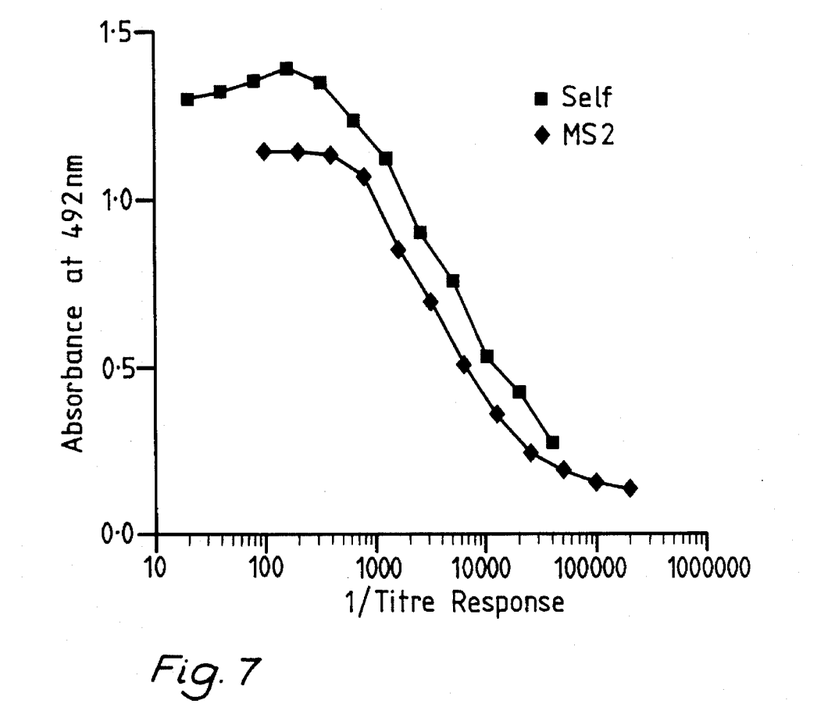
FIG. 7. Specificity of the 42 day serum sample against MS-2HA measured by ELISA using either MS-2HA capsids or wild type MS-2 capsids as antigen.

The 42 day samples from mice immunised with 500 μg of MS2-HA were analysed for specificity versus the inserted peptide. This was done again by ELISA assay using either self or the carrier, i.e. wild type MS-2 capsid empties as antigen. The results are shown in FIG. 7. Throughout the titration series there is a higher value for the assay against self. Titres at 50% saturation are 1:7,500 for self, versus 1:3,200 for MS-2 carrier, an indication that high specific antibody titres against the insert had been produced. The sera produced also cross-reacted with the HA9-mer peptide coupled to Keyhole Limpet Hemocyanin (KLH), although much less well, presumably because in this case the peptide is presented singly as a linear fragment.

Further immunogentcity assays were carried out by ELISA, on 54 day bleeds from Balb C mice immunised with MS2-HA prepared as described above with and without Alhydrogel adjuvant and wild type MS-2 with and without adjuvant. For comparison purposes assays were also carried out on 54 day bleeds from Balb C mice lmmunised with HA9-mer peptide coupled to KLH, with and without Alhydrogel adjuvant and a synthetic peptide encompassing the HA9-mer sequence alone with and without adjuvant. A 500 μg dose regime was employed. Alhydrogel when used was employed as a 1:1 mix. The results are shown in Table 1 below. The titres given are against "self", and "carrier". For the injections with MS2-HA and wild type MS-2, "self" is the MS2-HA construct while "carrier" is wild type MS-2. For the injections with KLH constructs, "self" is the KLH-HA9-mer construct and "carrier" is KLH. For the injections with HA9-mer peptide alone, "self" is HA9-mer peptide alone, there being no "carrier".

TABLE 1

| Injected Material | Reciprocal of Titre Against | |
|---|---|---|
| | a) "Self" | b) "Carrier" |
| MS-2-HA + Alhydrogel | 1500 | 600 |
| MS-2-HA | 4500 | 2500 |
| MS-2 + Alhydrogel | no reading | 2500 |
| MS-2 | 1800 | 5300 |
| KLH-HA9-mer + Alhydrogel | 4900 | 1800 |
| KLH-HA9-mer | 900 | 550 |
| HA9-mer + Alhydrogel | 33 | — |
| HA9-mer | 45 | — |

The results shown in Table 1 clearly demonstrate the specificity of antibody response to the HA9-mer constitutively expressed in the MS2-HA construct. Further it is also demonstrated that it may not always be necessary to use an adjuvant or carrier such as KLH in order to achieve a highly specific antibody response against a constitutively expressed foreign peptide such as the HA9-mer.

EXAMPLE 7

Antigenicity of MS2-IgE' in vivo.

In order to test the immunogenicity of the MS2-IgE' construct in rats, a sample of MS2-IgE' was prepared as follows:

Lysates of the construct were prepared as described in Example 5A except that the cells were grown at 30° C. and the resuspension buffer used was 50 mM Hepes+100 mM NaCl+10 mM DTT+5mM EDTA pH 7.4. Lysates were clarified by centrifugation.

After centrifugation pellets were resuspended in the same isolation buffer and the following extraction procedure was developed. The resuspended pellet was treated with DNase I (10 μg/μl) with the addition of magnesium acetate to 6 mM. After 30 min at 37° C. a salt extraction was carried out by the addition of NaCl to 50 mM for 20 min at 37° C. Next the sample was centrifuged at 10,000 rpm for 20 min at 4° C. and the pellet was resuspended in the same resuspension buffer (RS) but with the addition of 1% v/v Triton X-100+ 0.05% w/v Sodium Deoxycholate. Using a magnetic stirrer, the mixture was constantly stirred for 60 min on ice. The mixture was then centrifuged and resuspended in RS as above. Fluorotrichloromethane was added to the suspension (1:1) and the mixture was constantly stirred using a magnetic stirrer for 15 min at 4° C. The mixture was centrifuged at 3,000 rpm for 30 min at 4° C. and the top solubilised layer (SL) was aspirated and stored on ice while the interface phase was resuspended and the procedure was repeated five times. The pooled SL was ammonium sulphate concentrated, centrifuged and stored at 4° C. for further analysis.

The above prepared material was used to immunize two male Wistar rats (200 g) in accordance with the following two schedules:

1st Schedule: 0.25 ml of the suspension of MS2-IgE' construct was injected s.c. on both days 0 and 14. On day 36, 0.75 ml of a 2:1 mixture of construct suspension and Alhydrogel (incubated at room temperature for 20 min) was injected s.c. Serum was obtained following tall bleeding at days 21, 48 and 70 for ELISA assay.

2nd Schedule: 0.35 ml of a 2:1 mixture of construct suspension and Alhydrogel (incubated at room temperature for 20 min) was injected s.c. on both days 0 and 14. On day 36, 0.75 ml of construct suspension and Alhydrogel mixture was injected subcutaneously. Serum was obtained for ELISA assay following tail bleeding at days 21, 48 and 70.

The sera obtained as above were checked by ELISA against the injected immunogen MS2-IgE' by determining response against "self" (in this case MS2-IgE') and against carrier MS-2. The highest titres were, versus self (1st schedule, 70 day bleed and 2nd schedule 70 day bleed respectively) 1:50,000 and 1:70,000 and versus carrier (1st schedule 70 day bleed, 2nd schedule 70 day bleed respectively) 1:10,000 and 1:20,000.

The result demonstrates the specific nature of the antibody response obtained against the IgE' peptide expressed constitutively in the MS2-IgE' construct.

We claim:

1. A chimeric protein selected from the group consisting of a coat protein of bacteriophages MS-2, R17, fr, GA, Qβ and SP modified by an insertion of a foreign peptide epitope between amino acids 14 and 15 of the bacteriophage MS-2 coat protein or corresponding amino acids of the coat protein from bacteriophages R17, fr, GA, QB and SP.

2. A capsid comprising a chimeric protein of claim 1.

3. A vaccine preparation comprising a chimeric protein of claim 1.

4. A vaccine preparation comprising a capsid of claim 2.

* * * * *